United States Patent [19]

Prasad et al.

[11] Patent Number: 6,147,222
[45] Date of Patent: Nov. 14, 2000

[54] PROCESS FOR THE MANUFACTURE OF SULFONYLAMINOCARBONYL TRIAZOLINONES AND SALTS THEREOF UNDER PH CONTROLLED CONDITIONS

[75] Inventors: Vidyanatha A. Prasad, Leawood, Kans.; Klaus Jelich, Wuppertal, Germany

[73] Assignee: Bayer Corporation, Pittsburgh, Pa.

[21] Appl. No.: 09/472,672

[22] Filed: Dec. 27, 1999

[51] Int. Cl.[7] .................................................. C07D 249/12
[52] U.S. Cl. ............................................................. 548/263.4
[58] Field of Search ........................................... 548/263.4

[56] References Cited

U.S. PATENT DOCUMENTS

| | | | |
|---|---|---|---|
| 5,241,074 | 8/1993 | Daum et al. | 548/263.8 |
| 5,276,162 | 1/1994 | Muller et al. | 548/263.4 |
| 5,405,970 | 4/1995 | Daum et al. | 548/263.6 |
| 5,532,378 | 7/1996 | Daum et al. | 548/263.8 |
| 5,534,486 | 7/1996 | Müller et al. | 504/273 |
| 5,625,074 | 4/1997 | Daum et al. | 548/263.8 |
| 5,631,380 | 5/1997 | Haas et al. | 548/263.4 |
| 5,652,372 | 7/1997 | Muller et al. | 548/263.4 |
| 5,750,718 | 5/1998 | Müller et al. | 548/263.6 |
| 5,869,681 | 2/1999 | Müller et al. | 548/263.6 |

*Primary Examiner*—Patricia L. Morris
*Attorney, Agent, or Firm*—Joseph C. Gil

[57] ABSTRACT

The present invention relates to a process for manufacturing sulfonylaminocarbonyl triazolinones and salts thereof, which are herbicidally active compounds, wherein the improvement comprises conducting the conversion reaction of the sulfonylaminocarbonyl triazolinone to a salt thereof under pH controlled conditions. In particular, this invention relates to the conversion of a substituted triazolinone to a sulfonylaminocarbonyl triazolinone, and without the isolation of this intermediate product, the sulfonylaminocarbonyl triazolinone is then converted to a salt thereof.

14 Claims, No Drawings

PROCESS FOR THE MANUFACTURE OF SULFONYLAMINOCARBONYL TRIAZOLINONES AND SALTS THEREOF UNDER PH CONTROLLED CONDITIONS

TECHNICAL FIELD OF THE INVENTION

The present invention relates to a process for manufacturing sulfonylaminocarbonyl triazolinones and salts thereof, which are herbicidally active compounds, wherein the improvement comprises conducting the conversion reaction of the sulfonylaminocarbonyl triazolinone to a salt thereof under pH controlled conditions. In particular, this invention relates to the conversion of a substituted triazolinone to a sulfonylaminocarbonyl triazolinone, and with or without the isolation of this intermediate product, the sulfonylaminocarbonyl triazolinone is then converted to a salt thereof.

In a preferred embodiment of the invention, 5-methoxy-4-methyl-2,4-dihydro-3H-1,2,4-triazol-3-one (MMT) is converted to 4,5-dihydro-3-methoxy-4-methyl-5-oxo-N-[[2-(trifluoromethoxy)phenyl]sulfonyl]-1H-1,2,4-triazole-1-carboxamide (MSU), and the MSU is converted to a salt thereof. Further, in another preferred embodiment of the invention, 5-propoxy-4-methyl-1,4-dihydro-3H-1,2,4-triazol-3-one (PMT) is converted to 2-[[[(4,5-dihydro-4-methyl-5-oxo-3-propoxy-1H-1,2,4-traizol-1-yl)carbonyl]amino]sulfonyl]-benzoic acid methyl ester (PSU), and the PSU is converted to a salt thereof.

BACKGROUND OF THE INVENTION

Sulfonylaminocarbonyl triazolinones are well known in the art, as are processes for their preparation and use as herbicides. European Patent EP-A 341,489 discloses certain substituted sulfonylaminocarbonyl triazolinones having herbicidal properties. Further, U.S. Pat. Nos. 5,534,486 and 5,869,681 describe a process for producing sulfonylaminocarbonyl triazolinones which are bonded by oxygen. The process includes the reaction of a triazolinone with a sulfonamide derivative. U.S. Pat. No. 5,750,718 describes intermediates for herbicidal sulfonylaminocarbonyl triazolinones having substituents which are bonded by sulfur.

However, the known prior art processes produce sulfonylaminocarbonyl triazolinones in unsatisfactory yield and purity. Thus, there is a need in the art for a process to manufacture sulfonylaminocarbonyl triazolinones in high yield and purity.

BRIEF SUMMARY OF INVENTION

The present invention is related to a process for the preparation of a sulfonylaminocarbonyl triazolinone or a salt thereof. The process includes the reaction of a substituted triazolinone of the following general formula (I)

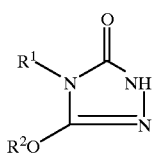

(I)

wherein
$R^1$ and $R^2$ each represents an unsubstituted or substituted alkyl, alkenyl, alkynyl, cycloalkyl, cycloalkylalkyl, aryl or arylalkyl radical, with a sulfonyl isocyanate of the following general formula (II)

$$O=C=N-SO_2-R^3 \quad (II)$$

wherein
$R^3$ represents an unsubstituted or substituted alkyl, aryl, arylalkyl or heteroaryl radical, to produce a sulfonylaminocarbonyl triazolinone intermediate product of the general formula (III)

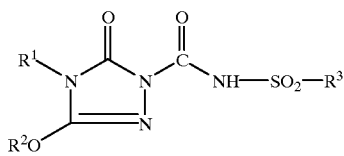

(III)

wherein $R^1$, $R^2$, and $R^3$ are as defined above.

The intermediate product is then reacted under pH controlled conditions with a base to produce a salt thereof, a final product of the general formula (IV)

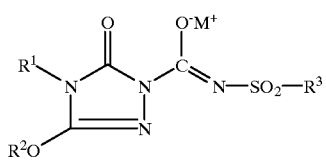

(IV)

wherein $R^1$, $R^2$, and $R^3$ are as defined above, and M represents an alkali or alkaline earth metal, or protonated ammonia derivative.

In an embodiment, the process of the invention is carried out in a one pot process, without isolating or separating the intermediate product (formula III). In another embodiment, the process is carried out in a two pot process, with the isolation or separation of the intermediate product (formula III).

DETAILED DESCRIPTION OF THE INVENTION

The present invention is related to a process for the preparation of sulfonylaminocarbonyl triazolinones and salts thereof. The process includes the reaction of a substituted triazolinone of the following general formula (I)

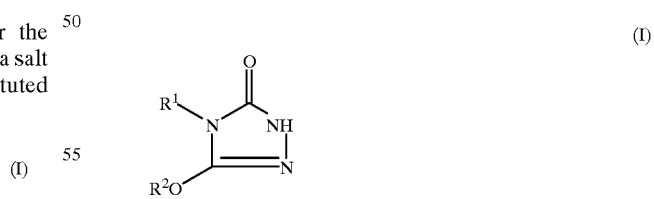

(I)

wherein
$R^1$ and $R^2$ each represents an unsubstituted or substituted alkyl, alkenyl, alkynyl, cycloalkyl, cycloalkylalkyl, aryl or arylalkyl radical, with a sulfonyl isocyanate of the following general formula (II)

$$O=C=N-SO_2-R^3 \quad (II)$$

wherein $R^3$ represents an unsubstituted or substituted alkyl, aryl, arylalkyl or heteroaryl radical, to produce a sulfonylaminocarbonyl triazolinone intermediate product of the general formula (II)

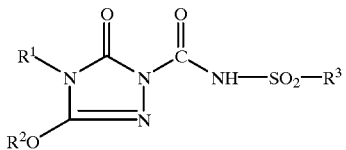

(III)

wherein $R^1$, $R^2$, and $R^3$ are as defined above.

The intermediate product is then reacted under pH controlled conditions with a base to produce a salt thereof, a final product of the general formula (IV)

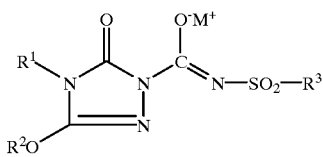

(IV)

wherein $R^1$, $R^2$, and $R^3$ are as defined above, and M represents an alkali or alkaline earth metal or protonated ammonia derivative.

The process of the invention may be carried out with or without isolating the intermediate product (formula III).

In a preferred embodiment of the invention, $R^1$ represents alkyl, alkenyl or alkynyl having in each case up to 6 carbon atoms, and each of which is unsubstituted or substituted by cyano, halogen, or $C_1$–$C_4$-alkoxy, or represents cycloalkyl group having 3 to 6 carbon atoms or cycloalkylalkyl group having 3 to 6 carbon atoms in the cycloalkyl moiety and 1 to 4 carbon atoms in the alkyl moiety, each of which is unsubstituted or substituted by halogen or $C_1$–$C_4$-alkyl, or represents aryl group having 6 or 10 carbon atoms or arylalkyl group having 6 or 10 carbon atoms in the aryl moiety and 1 to 4 carbon atoms in the alkyl moiety, each of which is unsubstituted or substituted by carboxyl, nitro, cyano, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxy-carbonyl.

More preferably, $R^1$ represents methyl, ethyl, n- or i-propyl, n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, cyclobutyl or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably, $R^1$ represents methyl.

In a preferred embodiment of the invention, $R^2$ represents alkyl, alkenyl or alkynyl, each of which has up to 6 carbon atoms, and each of which is unsubstituted or substituted by cyano, halogen or $C_1$–$C_4$-alkoxy, or represents cycloalkyl having 3 to 6 carbon atoms or cycloalkylalkyl having 3 to 6 carbon atoms in the cycloalkyl moiety and 1 to 4 carbon atoms in the alkyl moiety, each of which is unsubstituted or substituted by halogen or $C_1$–$C_4$-alkyl, or represents aryl having 6 to 10 carbon atoms or arylalkyl having 6 or 10 carbon atoms in the aryl moiety and 1 to 4 carbon atoms in the alkyl moiety, each of which is unsubstituted or substituted by carboxyl, cyano, nitro, halogen, $C_1$–$C_4$-alkyl, $C_1$–$C_4$-halogenoalkyl, $C_1$–$C_4$-alkoxy, $C_1$–$C_4$-halogenoalkoxy or $C_1$–$C_4$-alkoxycarbonyl.

More preferably, $R^2$ represents methyl, ethyl, n- or i-propyl or n-, i-, s- or t-butyl, each of which is unsubstituted or substituted by cyano, fluorine, chlorine or bromine, methoxy or ethoxy, or represents propenyl, butenyl, propinyl or butinyl, each of which is unsubstituted or substituted by cyano, fluorine, chlorine or bromine, or represents cyclopropyl, or cyclopropylmethyl, each of which is unsubstituted or substituted by fluorine, chlorine, bromine, methyl or ethyl, or represents phenyl or benzyl, each of which is unsubstituted or substituted by cyano, fluorine, chlorine, bromine, methyl, ethyl, trifluoromethyl, methoxy, ethoxy, difluoromethoxy, trifluoromethoxy, methoxycarbonyl or ethoxycarbonyl.

Most preferably, $R^2$ represents methyl, n- or i-propyl.

In a preferred embodiment of the invention.

$R^3$ represents the group

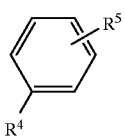

wherein $R^4$ and $R^5$ are identical or different and represent hydrogen, fluorine, chlorine, bromine, iodine, nitro, $C_1$–$C_6$-alkyl, which is unsubstituted or substituted by fluorine, chlorine, bromine, cyano, carboxyl, $C_1$–$C_4$-alkoxycarbonyl, $C_1$–$C_4$-alkylaminocarbonyl, di-($C_1$–$C_4$-alkyl)aminocarbonyl, hydroxyl, $C_1$–$C_4$-alkoxy, formyloxy, $C_1$–$C_4$-alkylcarbonyloxy, $C_1$–$C_4$-alkoxycarbonyloxy, $C_1$–$C_4$-alkylaminocarbonyloxy, $C_1$–$C_4$-alkylthio, $C_1$–$C_4$-alkylsulfinyl, $C_1$–$C_4$-alkylsulfonyl, di-($C_1$–$C_4$-alkyl)-aminosulfonyl, $C_3$–$C_6$-cycloalkyl or phenyl, or represent $C_2$–$C_6$-alkenyl which is unsubstituted or substituted by fluorine, chlorine, bromine, cyano, $C_1$–$C_4$-alkoxycarbonyl, carboxyl or phenyl, or represent $C_2$–$C_6$-alkynyl which is unsubstituted or substituted by fluorine, chlorine, bromine, cyano, $C_1$–$C_4$-alkoxycarbonyl, carboxyl or phenyl, or represent $C_1$–$C_4$-alkoxy which is unsubstituted or substituted by fluorine, chlorine, bromine, cyano, carboxyl, $C_1$–$C_4$-alkoxycarbonyl, $C_1$–$C_4$-alkoxy, $C_1$–$C_4$-alkylthio, $C_1$–$C_4$-alkylsulfinyl or $C_1$–$C_4$-alkylsulfonyl, or represent $C_1$–$C_4$-alkylthio which is unsubstituted or substituted by fluorine, chlorine, bromine, cyano, carboxyl, $C_1$–$C_4$-alkoxycarbonyl, $C_1$–$C_4$-alkylthio, $C_1$–$C_4$-alkylsulfinyl or $C_1$–$C_4$-alkylsulfonyl, or represent $C_3$–$C_6$ alkenyloxy which is unsubstituted or substituted by fluorine, chlorine, bromine, cyano or $C_1$–$C_4$-alkoxycarbonyl, or represent $C_2$–$C_6$-alkenylthio which is unsubstituted or substituted by fluorine, chlorine, bromine, cyano, nitro, $C_1$–$C_3$-aklylthio or $C_1$–$C_4$-alkoxycarbonyl, $C_3$–$C_6$-alkinyloxy, $C_3$–$C_6$-alkinylthio or the radical —S(O) P—$R^6$ where p represents the numbers 1 or 2 and $R^6$ represents $C_1$–$C_4$-alkyl which is unsubstituted or substituted by fluorine, chlorine, bromine, cyano or $C_1$–$C_4$-alkoxycarbonyl, $C_3$–$C_6$-alkenyl, $C_3$–$C_6$-alkinyl, $C_1$–$C_4$-alkoxy, $C_1$–$C_4$-alkoxy-$C_1$–$C_4$-alkylamino, $C_1$–$C_4$-alkylamino, di-($C_1$–$C_4$-alkyl)-amino, phenyl or the radical —NHOR$^7$ wherein $R^7$ represents $C_1$–$C_{12}$-alkyl which is unsubstituted or substituted by fluorine, chlorine, cyano, $C_1$–$C_4$-alkoxy, $C_1$–$C_4$-alkylthio, $C_1$–$C_4$-alkylsulfinyl, $C_1$–$C_4$-alkylsulfonyl, $C_1$–$C_4$-alkyl-carbonyl, $C_1$–$C_4$-alkoxycarbonyl, $C_1$–$C_4$-alkylaminocarbonyl or di-($C_1$–$C_4$-alkyl)-amino-carbonyl, or represents $C_3$–$C_6$-alkenyl which is unsubstituted or substituted by fluorine, chlorine or bromine, $C_3$–$C_6$-alkynyl, $C_3$–$C_6$-cycloalkyl, $C_3$–$C_6$-cycloalkyl-$C_1$–$C_2$-alkyl, phenyl-$C_1$–$C_2$-alkyl which is unsubstituted or substituted by fluorine, chlorine, nitro, cyano, $C_1$–$C_4$-alkyl, $C_1$–$C_4$-alkoxy or $C_1$–$C_4$-alkoxycarbonyl), or represents benzhydryl, or represents phenyl which is unsubstituted or substituted by fluorine, chlorine, nitro, cyano, $C_1$–$C_4$-alkyl, trifluoromethyl, $C_1$–$C_4$-alkoxy, $C_1$–$C_2$-fluoroalkoxy, $C_1$–$C_4$-alkylthio, trifluoromethylthio or $C_1$–$C_4$-alkoxycarbonyl, $R^4$ and/or $R^5$ furthermore represent phenyl or phenoxy, or represent $C_1$–$C_4$-alkylcarbonylamino, $C_1$–$C_4$-alkoxycarbonyl-amino, $C_1$–$C_4$-alkylamino-carbonyl-amino, di-($C_1$–$C_4$-alkyl)-amino-carbonyl-amino, or the radical —CO—$R^8$ wherein $R^8$ represents $C_1$–$C_6$-alkyl, $C_1$–$C_6$-alkoxy, $C_3$–$C_6$-cycloalkoxy, $C_3$–$C_6$-alkenyloxy, $C_1$–$C_4$-alkylthio, $C_1$–$C_4$-alkylamino, $C_1$–$C_4$-alkoxyamino, $C_1$–$C_4$-alkoxy-$C_1$14 $C_4$-alkyl-amino or di-($C_1$–$C_4$-alkyl)-amino which are unsubstituted or substituted by halogen selected from the group consisting of fluorine and chlorine, $R^4$ and/or $R^5$ furthermore represent trimethylsilyl, thiazolinyl, $C_1$–$C_4$-alkylsulfonyloxy, di-($C_1$–$C_4$-alkyl)-aminosulfonylamino or the radical —CH=N—$R^9$ wherein $R^9$ represents $C_1$–$C_6$-alkyl which is unsubstituted or substituted by fluorine, chlorine, cyano, carboxyl, $C_1$–$C_4$-alkoxy, $C_1$–$C_4$-alkylthio, $C_1$–$C_4$-alkylsulfinyl or $C_1$–$C_4$-alkylsulfonyl, or represents benzyl which is unsubstituted or substituted by fluorine or chlorine, or represents $C_3$–$C_6$-alkenyl or $C_3$–$C_6$-alkynyl, each of which is unsubstituted or substituted by fluorine or chlorine, or represents phenyl which is unsubstituted or substituted by fluorine, chlorine, bromine, $C_1$–$C_4$-alkyl, $C_1$–$C_4$-alkoxy, trifluoromethyl, trifluoromethoxy or trifluoromethylthio, or represents unsubstituted or halogen-substituted $C_1$–$C_6$-alkoxy, $C_3$–$C_6$-alkenoxy, $C_3$–$C_6$-alkinoxy or benzyloxy, wherein the halogen is selected from the group consisting of fluorine and chlorine, or represents amino, $C_1$–$C_4$-alkylamino, di-($C_1$–$C_4$-alkyl)-amino, phenylamino, $C_1$–$C_4$-alkyl-carbonylamino, $C_1$–$C_4$-alkoxy-carbonylamino or $C_1$–$C_4$-alkyl-sulfonylamino, or represents phenylsulfonylamino which is unsubstituted or substituted by fluorine, chlorine, bromine or methyl, furthermore $R^3$ represents the radical

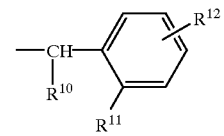

wherein $R^{10}$ represents hydrogen or $C_1$–$C_4$-alkyl, $R^{11}$ and $R^{12}$ are identical or different and represent hydrogen, fluorine, chlorine, bromine, nitro, cyano, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, carboxyl, $C_1$–$C_4$-alkoxy-carbonyl, dimethylaminocarbonyl, $C_1$–$C_4$-alkylsulfonyl or di-($C_1$–$C_4$-alkyl)-aminosulfonyl, furthermore $R^3$ represents the radical

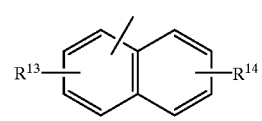

wherein $R^{13}$ and $R^{14}$ are identical or different and represent hydrogen, fluorine, chlorine, bromine, nitro, cyano, $C_1$–$C_4$-alkyl which is unsubstituted or substituted by halogen selected from the group consisting of fluorine and chlorine, or $C_1$–$C_4$-alkoxy which is unsubstituted or substituted by halogen selected from the group consisting of fluorine and chlorine, furthermore $R^3$ represents the radical

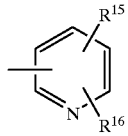

wherein $R^{15}$ and $R^{16}$ are identical or different and represent hydrogen, fluorine, chlorine, bromine, nitro, cyano, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, or represent $C_1$–$C_4$-alkylthio, $C_1$–$C_4$-alkylsulfinyl or $C_1$–$C_4$-alkylsulfonyl which are unsubstituted or substituted by halogen selected from the group consisting of fluorine and chlorine, or represent aminosulfonyl, mono-($C_1$–$C_4$-alkyl)-aminosulfonyl, di-($C_1$–$C_4$-alkyl)-aminosulfonyl or $C_1$–$C_4$-alkoxycarbonyl or dimethylaminocarbonyl;

furthermore $R^3$ represents the radical

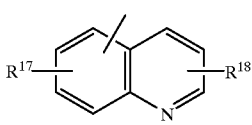

wherein $R^{17}$ and $R^{18}$ are identical or different and represent hydrogen, fluorine, chlorine, bromine, $C_1$–$C_4$-alkyl which is unsubstituted or substituted by halogen selected from the group consisting of fluorine and bromine, $C_1$–$C_4$-alkoxy which is unsubstituted or substituted by halogen selected from the group consisting of fluorine and chlorine, $C_1$–$C_4$-alkylthio, $C_1$–$C_4$-alkylsulfinyl or $C_1$–$C_4$-alkylsulfonyl which are unsubstituted or substituted by halogen selected from the group consisting of fluorine and chlorine, or represent di-($C_1$–$C_4$-alkyl)-aminosulfonyl;

furthermore $R^3$ represents the radical

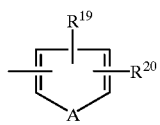

wherein $R^{19}$ and $R^{20}$ are identical or different and represent hydrogen, fluorine, chlorine, bromine, cyano, nitro, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, $C_1$–$C_4$-alkylthio, $C_1$–$C_4$-alkylsulfinyl or $C_1$–$C_4$-alkysulfonyl which is unsubstituted or substituted by halogen selected from the group consisting of fluorine and chlorine, di-($C_1$–$C_4$-alkyl)-aminosulfonyl, $C_1$–$C_4$-alkoxy-carbonyl or dimethylaminocarbonyl, and A represents oxygen, sulfur or the group N—$Z^1$, wherein $Z^1$ represents hydrogen, $C_1$–$C_4$-alkyl which is unsubstituted or substituted by fluorine, chlorine, bromine, or cyano, $C_3$–$C_6$-cycloalkyl, benzyl, phenyl which is unsubstituted or substituted by fluorine, chlorine, bromine or nitro, $C_1$–$C_4$-alkylcarbonyl, $C_1$–$C_4$-alkoxy-carbonyl or di-($C_1$–$C_4$-alkyl)-amino-carbonyl;

furthermore $R^3$ represents the radical

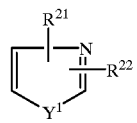

wherein $R^{21}$ and $R^{22}$ are identical or different and represent hydrogen, $C_1$–$C_4$-alkyl, halogen, $C_1$–$C_4$-alkoxycarbonyl, $C_1$–$C_4$-alkoxy or $C_1$–$C_4$-halogenoalkoxy, $Y^1$ represents sulfur or the group N—$R^{23}$ wherein $R^{23}$ represents hydrogen or $C_1$–$C_4$-alkyl;

furthermore $R^3$ represents the radical

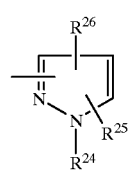

wherein $R^{24}$ represents hydrogen, $C_1$–$C_4$-alkyl, benzyl, pyridyl, quinolinyl or phenyl, $R^{25}$ represents hydrogen, halogen, cyano, nitro, $C_1$–$C_4$-alkyl which is unsubstituted or substituted by halogen selected from the group consisting of fluorine and chlorine, $C_1$–$C_4$-alkoxy which is unsubstituted or substituted by halogen selected from the group consisting of fluorine and chlorine, dioxolanyl or $C_1$–$C_4$-alkoxycarbonyl and $R^{26}$ represents hydrogen, halogen or $C_1$–$C_4$-alkyl;

furthermore $R^3$ represents a compound selected from the group consisting of

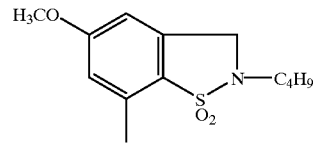

-continued

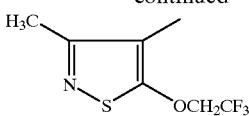 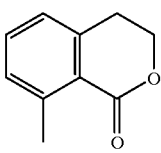

The invention furthermore preferably relates to the sodium, potassium, magnesium, calcium, ammonium, $C_1$–$C_4$-alkyl-ammonium, di-($C_1$–$C_4$-alkyl)-ammonium, tri-($C_1$–$C_4$-alkyl)-ammonium, $C_5$- or $C_6$-cycloalkyl-ammonium and di-($C_1$–$C_2$-alkyl)-benzyl-ammonium salts of the formula (IV) in which $R^1$, $R^2$ and $R^3$ have the meanings mentioned above as being preferred.

In particular, the invention relates to compounds of the formula (IV)
wherein
$R^1$ represents hydrogen, amino, $C_1$–$C_4$-alkyl which is unsubstituted or substituted by fluorine, cyano, methoxy or ethoxy, or represents allyl, $C_3$–$C_6$-cycloalkyl, benzyl, phenyl, $C_1$–$C_3$-alkylamino, $C_3$–$C_6$-cycloalkylamino or di-($C_1$–$C_3$-alkyl)-amino,
$R^2$ represents $C_1$–$C_4$-alkyl which is unsubstituted or substituted by halogen selected from the group consisting of fluorine and chlorine, methoxy or ethoxy, or represents $C_3$–$C_4$-alkenyl which is unsubstituted or substituted by halogen selected from the group consisting of fluorine and chlorine, or represents $C_3$–$C_6$-cycloalkyl, or represents benzyl which is unsubstituted or substituted by a compound selected from the group consisting of fluorine, chlorine and methyl, and
$R^3$ represents the group

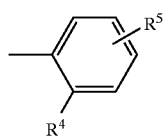

wherein
$R^4$ represents fluorine, chlorine, bromine, methyl, trifluoromethyl, methoxy, difluoromethoxy, trifluoromethoxy, 2-chloro-ethoxy, 2-methoxy-ethoxy, $C_1$–$C_3$-alkylthio, $C_1$–$C_3$-alkysulfinyl, $C_1$–$C_3$-alkylsulfonyl, dimethylaminosulfonyl, diethylaminosulfonyl, N-methoxy-N-methylaminosulfonyl, methoxyaminosulfonyl, phenyl, phenoxy or $C_1$–$C_3$-alkoxy-carbonyl and
$R^5$ represents hydrogen, fluorine, chlorine or bromine;
furthermore
$R^3$ represents the radical

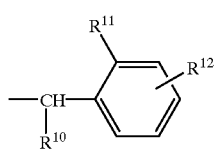

wherein
$R^{10}$ represents hydrogen,
$R^{11}$ represents fluorine, chlorine, bromine, methyl, methoxy, difluoromethoxy, trifluorormethoxy, ethoxy, methoxycarbonyl, ethoxycarbonyl, methylsulfonyl or dimethylaminosulfonyl and
$R^{12}$ represents hydrogen;
furthermore
$R^3$ represents the radical

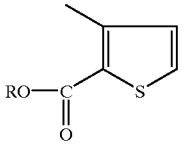

wherein
R represents $C_1$–$C_4$-alkyl, or represents the radical

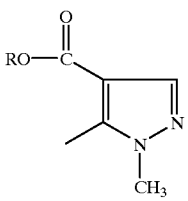

wherein
R represents $C_1$–$C_4$-alkyl.

The process of the invention may be conducted with or without isolating or separating the intermediate product of the formula (III).

The process according to the invention is generally carried out at atmospheric pressure. However, it is also possible to conduct the process under elevated or reduced pressure.

The reaction of the substituted triazolinone (formula I) with the sulfonyl isocyanate (formula II) to produce the sulfonylaminocarbonyl triazolinone intermediate product (formula III), is carried out at a temperature of from about −20° C. to about 120° C., and preferably at a temperature of from about 0° C. to about 45° C.

The reaction time to produce the intermediate product is up to about 48 hours, and preferably from about 1 hour to about 8 hours.

In the process of the invention, suitable sulfonyl isocyanates include 2-(trifluoromethoxy) benzensulfonyl isocyanate, 2-(methoxycarbonyl)benzenesulfonyl isocyanate, benzenesulfonyl isocyanate, p-toluenesulfonyl isocyanate, 2-fluoro, 2-chloro-, 2-bromo-, 2-methyl-, 2-methoxy-, 2-trifluoromethyl-, 2-difluoro-methoxy-, 2-trifluoromethoxy-, 2-methylthio-, 2-ethylthio-, 2-propylthio-, 2-methylsulfinyl-, 2-methyl-sulfonyl-, 2-dimethylaminosulfonyl-, 2-diethylamino-sulfonyl-, 2-(N-methoxy-N-methyl-aminosulfonyl-, 2-phenyl-, 2-phenoxy-, 2-methoxycarbonyl-, 2-ethoxycarbonyl, 2-propoxycarbonyl- and 2-isopropoxycarbonyl-phenylsulfonyl isocyanate, 2-fluoro-, 2-chloro-, 2-difluoromethoxy-, 2-trifluoro-methoxy-, 2-methoxycarbonyl- and 2-ethoxycarbonyl-benzylsulfonyl isocyanate, 2-methoxycarbonyl-3-thienyl-sulfonyl isocyanate, 4-methoxycarbonyl- and 4-ethoxy-carbonyl-1-methyl-pyrazol-5-yl-sulfonyl isocyanate.

In a preferred embodiment, the sulfonyl isocyanate is 2-(trifluoro-methoxy)-benzenesulfonyl isocyanate or 2-(methoxycarbonyl)-benzenesulfonyl isocyanate.

In an embodiment of the invention, the reaction of the substituted triazolinone (formula I) with the sulfonyl isocyanate (formula II) is carried out in the presence of a solvent.

Suitable solvents include inert organic solvents such as aliphatic and aromatic, unhalogenated and halogenated hydrocarbons such as pentane, hexane, heptane, cyclohexane, methylene chloride, ethylene chloride, benzene, toluene, xylene, chlorobenzene, dichlorobenzene, petroleum ether, hexane, cyclohexane, dichloromethane, chloroform, carbon tetrachloride; ethers such as diethyl ether, diisopropyl ether, dibutyl ether, dioxane, tetrahydrofuran or diglycol dimethyl ether, glycol dimethyl ether or ethylene glycol diethyl ether; ketones such as acetone, butanone, methyl ethyl ketone, methyl isopropyl ketone or methyl isobutyl ketone; nitriles such as acetonitrile, propionitrile or butyronitrile; amides such as N,N-dimethylformamide, N,N-dimethylacetamide, N-methylformanilide, N-methyl-pyrrolidone or hexamethylphosphoric triamide; esters such as methyl acetate or ethyl acetate; also dimethyl sulfoxide, tetramethylene sulfone and hexamethylphosphoric triamide.

Preferably, the solvent used in the process of the invention is methyl isobutyl ketone (MIBK), or xylene, or a commercially available mixture of xylenes containing ortho-xylene, para-xylene and meta-xylene.

The reaction of a sulfonylaminocarbonyl triazolinone intermediate product (formula III) with a base, to convert the intermediate product to a salt thereof (final product of the formula IV), is carried out at a temperature of from about −20° C. to about 120° C., and preferably from about 0° C. to about 45° C.

The reaction time to convert the intermediate product to the final product is up to about 48 hours, and preferably from about 2 hours to about 8 hours.

During this conversion step of the sulfonylaminocarbonyl triazolinone intermediate product (formula III) to a salt thereof (final product of the formula IV), the reaction is carried out under pH controlled conditions. Thus, the base is added to the reaction mixture in an amount such that the pH of the mixture attained is from about 5 to about 10, preferably from about 5.5 to about 9, and most preferably from about 6 to about 7.

Suitable bases for use in this conversion step include bases such as sodium hydroxide, potassium hydroxide, ammonia, or aqueous mixtures thereof. A preferred base is sodium hydroxide, or an aqueous solution of sodium hydroxide.

In an embodiment of the invention, the conversion of the intermediate product (formula III) to the final product (formula IV) is carried out in the presence of a solvent. Suitable solvents include aliphatic, alicyclic or aromatic, unhalogenated or halogenated hydrocarbons such as benzene, toluene, xylene, chlorobenzene, dichlorobenzene, petroleum ether, hexane, cyclohexane, dichloromethane, chloroform, tetrachloromethane; ethers such as diethyl ether, diisopropyl ether, dioxane, tetrahydrofuran or ethylene glycol dimethyl ether or ethylene glycol diethyl ether; ketones such as acetone, butanone, or methyl isobutyl ketone; nitriles such as acetonitrile, propionitrile or benzonitrile; amides such as N,N-dimethylformamide, N,N-dimethylacetamide, N-methylformanilide, N-methylpyrrolidone or hexamethylphosphoric triamide; esters such as methyl acetate or ethyl acetate, sulfoxides such as dimethyl sulfoxide, alcohols such as methanol, ethanol, n- or i-propanol, n-, i-, s-, or t-butanol, ethylene glycol monomethyl ether, ethylene glycol monoethyl ether, diethylene glycol monomethyl ether, diethylene glycol monoethyl ether; water and mixtures thereof. Preferred solvents include water, methyl isobutyl ketone, propanol, methanol, toluene, a commercially available mixture of xylenes containing ethylbenzene, ortho-xylene, para-xylene, meta-xylene, and mixtures thereof.

In a preferred embodiment of this invention, the conversion of the intermediate product (formula III) to the final product (formula IV) is carried out in a mixture of water and methyl isobutyl ketone, or a mixture of water, methanol and xylenes.

In a preferred embodiment of the invention, 5-methoxy-4-methyl-2,4-dihydro-3H-1,2,4-triazol-3-one (MMT) is converted to 4,5-dihydro-3-methoxy-4-methyl-5-oxo-N-[[2-(trifluoromethoxy)phenyl]sulfonyl]-1H-1,2,4-triazole-1-carboxamide (MSU), and the MSU is converted to a salt thereof. Further, in another preferred embodiment of the invention, 5-propoxy-4-methyl-1,4-dihydro-3H-1,2,4-triazol-3-one (PMT) is converted to 2-[[[(4,5-dihydro-4-methyl-5-oxo-3-propoxy-1H-1,2,4-triazol-1-yl)carbonyl]amino]sulfonyl]-benzoic acid methyl ester (PSU), and the PSU is converted to a salt thereof.

In another embodiment of the invention, the salt of the MSU is isolated as a monohydrate.

The invention is further illustrated but is not intended to be limited by the following examples in which all parts and percentages are by weight unless otherwise specified.

EXAMPLES

Example 1

The Preparation of MKH 6561-PSU Isolated

In a 1000 ml flask with mechanical stirrer and thermometer, 119.8 grams (0.2 moles) of isolated PSU and 200 ml of methyl isobutyl ketone (MIBK) were charged. The mixture was agitated and then 10 ml of water was added. The initial pH of the reaction mixture was 2.8. Then 50% sodium hydroxide (NaOH) was added to ambient temperature over a 2 hour time period, at pH controlled conditions. During this addition step, the pH of the reaction mixture was from about 4.6 to about 4.8. The pH of the reaction mixture stabilized at about 7.7. The mixture was agitated from about 1 hour and the solids were isolated by vacuum filtration. The net yield based on PSU was 97.5%.

Example 2

The Preparation of MKH 6562 Hydrate-MSU Not Isolated 261.0 grams (1.74 moles) of 98% pure 5-methoxy-4-methyl-2,4-dihydro-3H-1,2,4-triazol-3-one (MMT) hydrate in about 2600 grams of methyl isobutyl ketone (MIBK) was dried by azeotropic distillation of part of the MIBK under reduced pressure (with a pot temperature of about 80° C.) and then cooled to room temperature under a nitrogen atmosphere. To the resulting MMT slurry in MIBK was added 534.0 grams (1.74 moles) of 87.0% pure 2-(trifluoromethoxy) benzenesulfonyl isocyanate over a period of about 2 hours. The reaction mixture was stirred at room temperature for about 6 hours. The conversion reaction of the MMT (to MSU) was monitored using a liquid chromatograph. About 140.0 grams of water were added to the reaction mixture. The mixture was then treated with 50% aqueous sodium hydroxide (NaOH). The NaOH was added over a period of about 4 hours in an amount such that the pH of the reaction mixture was between about 6 and about 7. The reaction mixture was stirred for about 1 hour. The mixture was then filtered, and washed with about 500 grams of MIBK and dried to isolate the MKH 6562 hydrate. The yield of MKH 6562 hydrate was about 93.0% based on MMT hydrate. The purity (water free) was about 98.0%.

Example 2A

The procedure described in Example 2 was carried out with the exception that the 50% aqueous NaOH was added in an amount such that the pH of the reaction mixture was between about 10.2 and about 10.5. The purity of the MKH 6562 hydrate decreased to about 96.5%.

Example 2B

The procedure described in Example 2 was carried out with the exception that the 50% aqueous NaOH was added in an amount such that the pH of the reaction mixture was between about 11.0 and about 11.5. The purity of the MKH 6562 hydrate decreased to about 95.6%.

Example 2C

The procedure described in Example 2 was carried out with the exception that the 50% aqueous NaOH was added in an amount such that the pH of the reaction mixture attained was between about 12.0 and about 12.5. The purity of the MKH 6562 hydrate decreased to about 95.1%.

In Examples 2A, 2B, and 2C, concentrated $H_2SO_4$ was added to the reaction mixture in an amount such that the pH was about 7.0. The purity of the MKH then increased to about 98.0%.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for preparing a sulfonylaminocarbonyl triazolinone or a salt thereof, comprising the steps of:

a) reacting a substituted triazolinone of the following general formula (I)

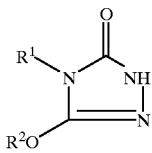

(I)

wherein $R^1$ and $R^2$ each represents an unsubstituted or substituted alkyl, alkenyl, alkynyl, cycloalkyl, cycloalkylalkyl, aryl or arylalkyl radical, with a sulfonyl isocyanate of the following general formula (II)

(II)

wherein $R^3$ represents an unsubstituted or substituted alkyl, aryl, arylalkyl or heteroaryl radical, to produce a sulfonylaminocarbonyl triazolinone intermediate product of the general formula (III)

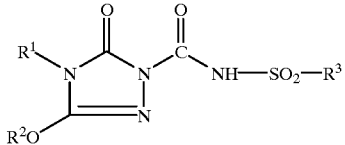

(III)

wherein $R^1$, $R^2$, and $R^3$ are as defined above, and b) reacting the intermediate product under pH controlled conditions with a base to produce a salt thereof, a final product of the general formula (IV)

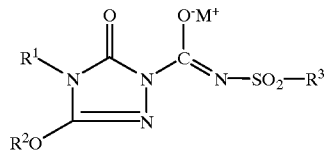

(IV)

wherein $R^1$, $R^2$, and $R^3$ are as defined above, and M represents an alkali or alkaline earth metal, or protonated ammonia derivative.

2. The process of claim 1 wherein the reaction in steps a) and b) is carried out at a temperature of from about −20° C. to about 120° C.

3. The process of claim 1 wherein the reaction in steps a) and b) is carried out at a temperature of from about 0° C. to about 45° C.

4. The process of claim 1 wherein the reaction in step a) is carried out in the presence of a solvent.

5. The process of claim 4 wherein the solvent is selected from the group consisting of aliphatic and aromatic unhalogenated and halogenated hydrocarbons, ethers, ketones, nitriles, amides, esters, dimethyl sulphoxide, tetramethylene sulfone and hexamethylphosphoric triamide.

6. The process of claim 1 wherein the sulfonyl isocyanate is selected from the group consisting of 2-(trifluoromethoxy) benzenesulfonyl isocyanate or 2-(methoxycarbonyl) benzenesulfonyl isocyanate.

7. The process of claim 1 wherein the base recited in step b) is selected from the group consisting of sodium hydroxide, potassium hydroxide, ammonia, and aqueous mixtures thereof.

8. The process of claim 7 wherein the base is selected from the group consisting of sodium hydroxide, potassium hydroxide, and aqueous mixtures thereof.

9. The process of claim 1 wherein the solvent recited in step b) is selected from the group consisting of aliphatic, alicyclic and aromatic, unhalogenated or halogenated hydrocarbons, ethers, ketones, nitrites, amides, esters, alcohols, water and mixtures thereof.

10. The process of claim 9 wherein the solvent is a mixture of methyl isobutyl ketone and water.

11. The process of claim 9 wherein the solvent is a mixture of xylenes, methanol and water.

12. The process of claim 1 wherein 5-methoxy-4-methyl-2,4-dihydro-3H-1,2,4-triazol-3-one (MMT) is converted to 4,5-dihydro-3-methoxy-4-methyl-5-oxo-N-[[2-(trifluoromethoxy)phenyl]sulfonyl]-1H-1,2,4-triazole-1-carboxamide (MSU), and the MSU is converted to a salt thereof.

13. The process of claim 12 further comprising the step of isolating the MSU salt thereof as a monohydrate.

14. The process of claim 1 wherein the reaction in steps a) and b) is carried out in a one pot process, without isolation of the intermediate product of formula (III).

* * * * *